(12) United States Patent
Zhang

(10) Patent No.: US 8,748,453 B2
(45) Date of Patent: Jun. 10, 2014

(54) SUBSTITUTED HETEROCYCLIC COMPOUNDS AS KINASES INHIBITORS AND METHODS OF USE THEREOF

(75) Inventor: Dawei Zhang, Thousand Oaks, CA (US)

(73) Assignee: Medolution Limited, Admiralty (HK)

( * ) Notice: Subject to any disclaimer, the term of this patent is extended or adjusted under 35 U.S.C. 154(b) by 144 days.

(21) Appl. No.: 13/380,693

(22) PCT Filed: Jun. 24, 2010

(86) PCT No.: PCT/US2010/039877
§ 371 (c)(1),
(2), (4) Date: Dec. 23, 2011

(87) PCT Pub. No.: WO2010/151710
PCT Pub. Date: Dec. 29, 2010

(65) Prior Publication Data
US 2012/0101116 A1 Apr. 26, 2012

Related U.S. Application Data

(60) Provisional application No. 61/269,525, filed on Jun. 25, 2009.

(51) Int. Cl.
*A01N 43/42* (2006.01)
*A61K 31/44* (2006.01)
*C07D 215/00* (2006.01)

(52) U.S. Cl.
USPC .......................................... 514/299; 546/152

(58) Field of Classification Search
USPC .................................. 546/152; 514/311, 299
See application file for complete search history.

(56) References Cited

U.S. PATENT DOCUMENTS 6,002,008 A    12/1999  Wissner et al.

OTHER PUBLICATIONS

Hai-Feng Chen, Computational Study of the Binding Mode of Epidermal Growth Factor Receptor Kinase Inhibitors, Chem. Biol. Drug Des., 2008, 434-446, v. 71.
Mazal Shaul, et al., Novel iodine-124 labeled EGFR inhiitors as potential PET agents for molecular imaging in cancer, Bioorg. Med. Chem., 2004, 3421-3429, v. 12.
Amor A. San Juan, Towards predictive inhibitor design for the EGFR autophosphorylation activity, Eur. J. Med. Chem., 2008, 781-791, v. 43.
Deepa V. Pendekar et al., 3D QSAR studies of inhibitors of epidermal growth factor receptor [EGFR] using CoMFA and GFA methodologies, Med. Chem. Res., 2004, 605-618, v.13.
Allan Wissner et al., Synthesis and Structure-activity Relationships of 6,7-Disustituted 4-Anilinoquinoline-3-carbonitriles. J. Med. Chem., 2003, 49-63, v. 46.

*Primary Examiner* — Paul V. Ward
(74) *Attorney, Agent, or Firm* — Feng Tian

(57) ABSTRACT

The present invention is directed to novel quinolines and quniazolines, their derivatives, pharmaceutically acceptable salts, solvates and hydrates thereof which are useful for the treatment of protein kinases mediated diseases and conditions. The compounds of this invention have a general Formula (I) wherein $R^1$ to $R^{11}$ and X are defined herein.

12 Claims, No Drawings

SUBSTITUTED HETEROCYCLIC COMPOUNDS AS KINASES INHIBITORS AND METHODS OF USE THEREOF

CROSS REFERENCE TO RELATED APPLICATION

The application is a 35 U.S.C. §371 national stage application of International Patent Application PCT/US2010/039877 (published as WO 2010/151710 A2), filed Jun. 24, 2010, which claimed priority of U.S. Provisional Application No. 61/269,525, filed Jun. 25, 2009, the contents of which are hereby incorporated by reference in their entirety.

FIELD OF THE INVENTION

The present invention is directed to novel quinoline and quinazoline kinase inhibitors, and their pharmaceutically acceptable salts, solvates, hydrates, prodrugs and metabolites thereof, the preparation thereof, and the use of such compounds to treat kinase mediated diseases and conditions such as cancer.

BACKGROUND OF THE INVENTION

Protein kinases represent a large family of enzymes, which catalyze the phosphorylation of target protein substrates. The phosphorylation is usually a transfer reaction of a phosphate group from ATP to the protein substrate. Common points of attachment for the phosphate group to the protein substrate include, for example, a tyrosine, serine or threonine residue. Examples of kinases in the protein kinase family include, without limitation, abl1 (v-abl Abelson murine leukemia viral oncogene homolog 1), Akt, Alk, bcr-abl1, c-kit, c-Met, c-src, c-fms, CDK1-10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Fyn, Hck, IGF-1R, Jak, KDR, Lck, Lyn, MEK, PDGFR, PIK, PKC, PYK2, ros, tie, tie2, TRK, Yes, and Zap70. Due to their activity in numerous cellular processes, kinases have emerged as important therapeutic targets.

Epidermal growth factor (EGF) is a widely distributed growth factor that in cancer, can stimulate cancer-cell proliferation, block apoptosis, activate invasion and metastasis, and stimulate angiogenesis (Citri, et al., *Nat. Rev. Mol. Cell. Biol.* 7:505, 2006; Hynes, et al., *Nat. Rev. Cancer* 5:341, 2005). The EGF receptor (EGFR or ErbB) is a transmembrane, tyrosine kinase receptor that belongs to a family of four related receptors. The majority of human epithelial cancers are marked by functional activation of growth factors and receptors of this family (Ciardiello, et al., *New Eng. J. Med.* 358: 1160, 2008) so that EGF and EGFR are natural targets for cancer therapy.

One member of the EGFR family is ErbB2 (also referred to as the neu or HER-2). The ErbB2 gene is often found amplified in breast or ovarian cancer and in glioblastoma. Over expression of ErbB2 has been demonstrated to lead to increased tumorigenicity, tumor invasiveness, increased metastatic potential, and altered sensitivity to hormonal and chemotherapeutic agents in transfection studies in cellular and animal models (Pegram, et al., *Oncogene*, 15, 537-547, 1997).

SUMMARY OF THE INVENTION

In one aspect, the present invention provides compounds of Formula I:

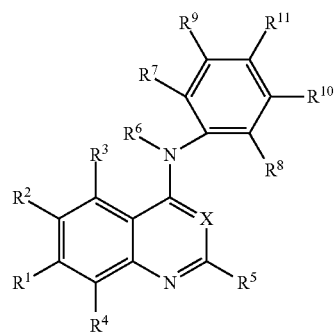

or their pharmaceutically acceptable salts, solvates, or prodrugs, or metabolites thereof, wherein $R^1$ and $R^2$ are independently selected from hydrogen, deuterium, halogen, trifluoromethyl, optionally substituted alkoxy, optionally substituted deuterated alkoxy and optionally substituted aminocarbonyl;

X is N or C—CN;

$R^3$ to $R^6$ are independently hydrogen (H) or deuterium (D);

$R^7$-$R^{10}$ are independently selected from hydrogen, deuterium, $CH_3$, $CD_3$, $CH_2D$, $CHD_2$, halogen, cyano, trifluoromethyl, optionally substituted alkoxy, optionally substituted deuterated alkoxy, optionally substituted $C_2$-$C_6$ alkynyl and optionally substituted deuterated $C_2$-$C_6$ alkynyl; and $R^{11}$ is hydrogen, deuterium, halogen, trifluoromethyl, optionally substituted alkoxy, optionally substituted deuterated alkoxy, optionally substituted aminocarbonyl, or urea;

provided that $R^1$ to $R^{11}$ contain at least one deuterium atom.

In another aspect, herein provides compounds of Formula II:

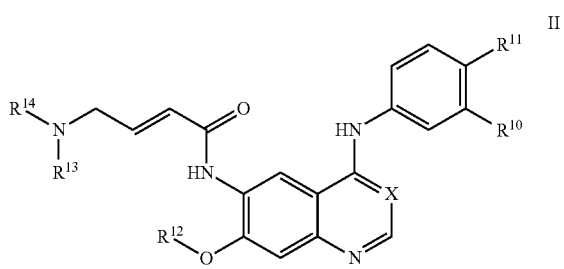

or their pharmaceutically acceptable salts, solvates or prodrugs or metabolites thereof, wherein X is N or C—CN;

$R^{10}$ is selected from hydrogen, deuterium, $CH_3$, $CD_3$, $CH_2D$, $CHD_2$, F, Cl, $CF_3$, CN, ethynyl and ethynyl-d;

$R^{11}$ is selected from hydrogen, deuterium, $CH_3$, $CD_3$, $CH_2D$, $CHD_2$, F, Cl, $CF_3$, 3-fluorobenzyloxy, and pyridin-2-ylmethoxy;

$R^{12}$ is selected methoxy, methoxy-$d_3$, ethoxy, ethoxy-$d_3$, 2-methoxyethoxy, and 2-methoxy-$d_3$-ethoxy;

$R^{13}$ and $R^{14}$ are independently selected from hydrogen, deuterium, $CH_3$, $CD_3$, $CH_2D$, and $CHD_2$; and provided that $R^{10}$ to $R^{14}$ contain at least one deuterium atom.

In another aspect, herein provides compounds of Formula III:

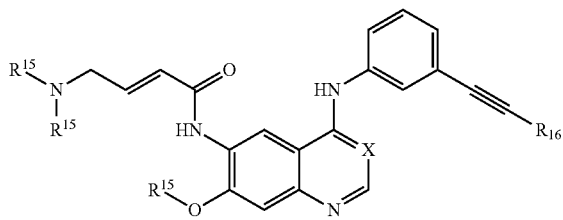

or their pharmaceutically acceptable salts, solvates or prodrugs or metabolites thereof, wherein
X is N or C—CN;
$R^{15}$ is $C_1$-$C_6$ alkyl or $C_1$-$C_6$ deuterated alkyl; and
$R^{16}$ is hydrogen or deuterium.

In another aspect, the present invention provides pharmaceutical compositions comprising a compound of Formulas I-III and a pharmaceutically acceptable carrier.

In another aspect, herein provides methods for regulating the tyrosine kinase signaling transduction comprising administrating to a mammalian subject a therapeutically effective amount of invention compounds. Methods for treating or preventing an EGFR and/or ErbB2 mediated disorder or for treating neoplasia or for treating or preventing a hyper-proliferative and/or angiogenesis are also provided herein.

DETAILED DESCRIPTION OF THE INVENTION

Certain kinase inhibitors are known in the art. HKI272 is one of such compounds. The carbon-hydrogen bonds of these compounds contain a naturally occurring distribution of hydrogen isotopes, namely $^1H$ or protium (about 99.9844%), $^2H$ or deuterium (about 0.0156%), and $^3H$ or tritium (in the range between about 0.5 and 67 tritium atoms per $10^{18}$ protium atoms). Increased levels of deuterium incorporation produce a detectable Kinetic Isotope Effect (KIE) that could affect the pharmacokinetic, pharmacologic and/or toxicological parameters of such anti-neoplastic agents relative to compounds having naturally occurring levels of deuterium. Some aspects of the present invention disclosed herein describe a novel approach to designing and synthesizing new analogs of these anti-neoplastic agents through chemical modifications and derivations of the carbon-hydrogen bonds of these anti-neoplastic agents and/or of the chemical precursors used to synthesize the anti-neoplastic agents. Certain modifications of certain carbon-hydrogen bonds to carbon-deuterium bonds, in some embodiments, generate novel anti-neoplastic agents with improved pharmacological, pharmacokinetic and/or toxicological properties in comparison to the non-isotopically enriched anti-neoplastic agents. In some embodiments, deuterium incorporation levels in compounds of the invention are significantly higher than the naturally-occurring levels.

Various deuteration patterns are used to a) reduce or eliminate unwanted metabolites, b) adjust the half-life of the parent drug, and/or c) decrease the production of deleterious metabolites in specific tissues and create a more effective drug and a safer drug for polypharmacy, whether the polypharmacy be intentional or not. The deuteration approach has strong potential to slow the metabolism via various oxidative mechanisms.

In some embodiments, the deuterated analogs of this invention uniquely maintain the beneficial aspects of the non-isotopically enriched drugs while substantially increasing the maximum tolerated dose, decreasing toxicity, increasing the half-life ($T_{1/2}$), lowering the maximum plasma concentration ($C_{max}$) of the minimum efficacious dose (MED), lowering the efficacious dose and thus decreasing the non-mechanism-related toxicity, and/or lowering the probability of drug-drug interactions. In certain embodiments, some of the invention compounds also have strong potential to reduce the cost-of-goods (COG) owing to the ready availability of inexpensive sources of deuterated reagents combined with previously mentioned potential for lowering the therapeutic dose.

Deuterium (D or $^2H$) is a non-radioactive, stable isotope of hydrogen, the natural abundance of deuterium is 0.015%. Compound should be considered to be unnatural, if its level of deuterium has been enriched to be greater than their natural abundance level 0.015%.

In some compounds of this invention, it is understood that the abundance of deuterium is substantially greater than the natural abundance of deuterium, which is 0.015%, when a particular position is designated as deuterium. A position designated as deuterium typically has a minimum isotopic enrichment factor of at least 3000 at each atom designated as deuterium in said compound. The concentration of naturally abundant stable hydrogen is small and immaterial compared to the degree of stable isotopic substitution of compounds of this invention.

In some embodiments of the present invention, there are provided compounds of Formula I:

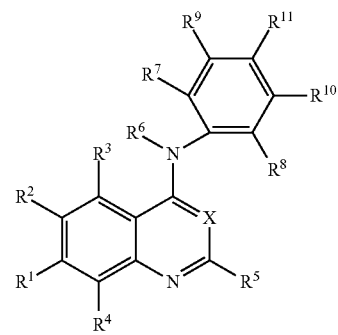

or their pharmaceutically acceptable salts, solvates, or prodrugs, or metabolites thereof, wherein
$R^1$ and $R^2$ are independently selected from hydrogen, deuterium, halogen, trifluoromethyl, optionally substituted alkoxy, optionally substituted deuterated alkoxy and optionally substituted aminocarbonyl;
X is N or C—CN;
$R^3$ to $R^6$ are independently hydrogen (H) or deuterium (D);
$R^7$-$R^{10}$ are independently selected from hydrogen, deuterium, $CH_3$, $CD_3$, $CH_2D$, $CHD_2$, halogen, cyano, trifluoromethyl, optionally substituted alkoxy, optionally substituted deuterated alkoxy, optionally substituted $C_2$-$C_6$ alkynyl and optionally substituted deuterated $C_2$-$C_6$ alkynyl; and
$R^{11}$ is hydrogen, deuterium, halogen, trifluoromethyl, optionally substituted alkoxy, optionally substituted deuterated alkoxy, optionally substituted aminocarbonyl, or urea;
provided that $R^1$ to $R^{11}$ contain at least one deuterium atom.

In some embodiments provide the compound of Formula I, wherein $R^1$ and $R^2$ are independently selected from optionally substituted alkoxy, optionally substituted deuterated alkoxy, and optionally substituted aminocarbonyl. In certain embodiments, $R^1$ is optionally substituted $C_1$-$C_8$ alkoxy. In certain embodiments, $R^1$ is methoxy, ethoxy or 2-methoxyethoxy. In certain embodiments, $R^1$ is $CD_3O—$, $CD_3CH_2O—$ or $CD_3OCH_2CH_2O—$. In other embodiments, $R^2$ is optionally substituted aminocarbonyl. In some embodiments, $R^1$ is aminocarbonyl and $R^2$ is alkoxy or deuterated alkoxy. In certain embodiments, $R^2$ is $CD_3O—$, $CD_3CH_2O—$ or $CD_3OCH_2CH_2O—$. In other embodiments, $R^2$ is 4-(dimethyl-$d_6$-amino)-2-butenamide. In some embodiments, $R^3$ to $R^8$ is hydrogen (H) or deuterium (D). In certain embodiments, $R^7$ and $R^8$ are independently F or Cl.

In some embodiments provide the compounds of Formula I, wherein $R^9$ and $R^{10}$ are independently selected from halogen, optionally substituted $C_2$-$C_6$ alkynyl and optionally substituted deuterated $C_2$-$C_6$ alkynyl. In certain embodiments, $R^9$ or $R^{10}$ is Cl.

In some embodiments provide the compounds of Formula I, wherein $R^{11}$ is substituted benzyloxy or pyridinylmethoxy. In certain embodiments, $R^{11}$ is benzyloxy where the phenyl ring is substituted with one to four halogens. In other embodiments, $R^{11}$ is pyridinylmethoxy.

In some embodiments, provided herein compounds of Formula II

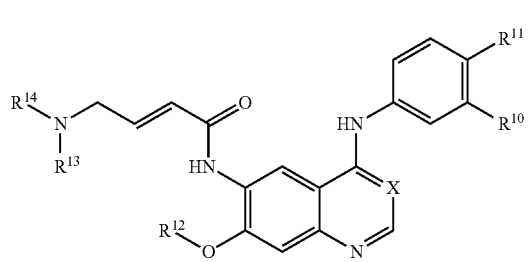

or their pharmaceutically acceptable salts, solvates, or prodrugs or metabolites thereof, wherein
X is N or C—CN;
$R^{10}$ is selected from hydrogen, deuterium, $CH_3$, $CD_3$, $CH_2D$, $CHD_2$, F, Cl, $CF_3$, CN, ethynyl and ethynyl-d;
$R^{11}$ is selected from hydrogen, deuterium, $CH_3$, $CD_3$, $CH_2D$, $CHD_2$, F, Cl, $CF_3$, 3-fluorobenzyloxy, and pyridin-2-ylmethoxy;
$R^{12}$ is selected methoxy, methoxy-$d_3$, ethoxy, ethoxy-$d_3$, 2-methoxyethoxy, and 2-methoxy-$d_3$-ethoxy;
$R^{13}$ and $R^{14}$ are independently selected from hydrogen, deuterium, $CH_3$, $CD_3$, $CH_2D$, and $CHD_2$; and
provided that $R^{10}$ to $R^{14}$ contain at least one deuterium atom.

In some embodiments provide compounds of Formula II wherein $R^{10}$ is Cl, ethynyl or ethynyl-d. In certain embodiments, $R^{10}$ is F, Cl or $CF_3$. In some embodiments, $R^{10}$ is ethynyl. In certain embodiments, $R^{10}$ is ethynyl-d. In some embodiments, $R^{11}$ is 3-fluorobenzyloxy or pyridin-2-ylmethoxy. In certain embodiments, $R^{11}$ is 3-fluorobenzyloxy. In other embodiments, $R^{11}$ is pyridin-2-ylmethoxy.

In some embodiments, provide herein compounds of Formula II, wherein $R^{12}$ is optionally substituted alkyl (such as $C_{1-8}$ alkyl) or optionally substituted deuterated alkyl. In certain embodiments, $R^{12}$ is selected from methoxy, methoxy-$d_3$, ethoxy, ethoxy-$d_3$, 2-methoxyethoxy, and 2-methoxy-$d_3$-ethoxy. In certain embodiments, $R^{12}$ is methyl, ethyl or 2-methoxyethyl. In other embodiments, $R^{12}$ is —$CD_3$, —$CH_2CD_3$ or —$CH_2CH_2OCD_3$.

In some embodiments provide compounds of Formula II, wherein $R^{13}$ and $R^{14}$ are independently selected from $CH_3$, and $CD_3$. In certain embodiments, $R^{13}$ is $CH_3$. In certain embodiments, $R^{13}$ is $CD_3$. In certain embodiments, $R^{14}$ is $CH_3$. In certain embodiments, $R^{14}$ is $CD_3$.

In another aspect, herein provides compounds of Formula III:

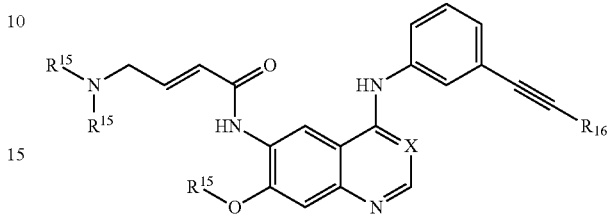

or their pharmaceutically acceptable salts, or solvates, or prodrugs or metabolites thereof, wherein
X is N or C—CN;
$R^{15}$ is $C_1$-$C_6$ alkyl or $C_1$-$C_6$ deuterated alkyl; and
$R^{16}$ is hydrogen or deuterium In some embodiments provide compounds of Formula III, wherein $R^{15}$ is $CD_3$, $CH_2CD_3$ or $CH_2CH_2OCD_3$. In other embodiments, $R^{15}$ is $CH_3$, $CH_2CH_3$ or $CH_2CH_2OCH_3$. In certain embodiments $R^{15}$ is $CH_3$ or $CD_3$. In some embodiments, $R^{16}$ is hydrogen. In some embodiments, $R^{16}$ is deuterium.

In some embodiments, there are provided without limitation exemplary compounds or their pharmaceutically acceptable salts, solvates, or prodrugs, or metabolites thereof, such as:

(E)-N-(4-(3-chloro-4-(pyridin-2-ylmethoxy)phenylamino)-7-ethoxyquinazolin-6-yl)-4-(dimethyl-$d_6$-amino)but-2-enamide, (E)-N-(4-(3-chloro-4-(pyridin-2-ylmethoxy)phenylamino)-3-cyano-7-ethoxyquinolin-6-yl)-4-(dimethyl-$d_6$-amino)but-2-enamide, (E)-N-(4-(3-chloro-4-(pyridin-2-ylmethoxy)phenylamino)-7-ethoxyquinazolin-6-yl)-4-(methyl-$d_3$-methylamino)but-2-enamide, (E)-N-(4-(3-chloro-4-(pyridin-2-ylmethoxy)phenylamino)-3-cyano-7-ethoxyquinolin-6-yl)-4-(methyl-$d_3$-(methyl)amino)but-2-enamide, (E)-N-(4-(3-chloro-4-(3-fluorobenzyloxy)phenylamino)-7-ethoxyquinazolin-6-yl)-4-(methyl-$d_3$-(methyl)amino)but-2-enamide, (E)-N-(4-(3-chloro-4-(3-fluorobenzyloxy)phenylamino)-3-cyano-7-ethoxyquinolin-6-yl)-4-(methyl-$d_3$-(methyl)amino)but-2-enamide, (E)-N-(4-(3-chloro-4-(3-fluorobenzyloxy)phenylamino)-7-ethoxyquinazolin-6-yl)-4-(dimethyl-$d_6$-amino)but-2-enamide, (E)-N-(4-(3-chloro-4-(3-fluorobenzyloxy)phenylamino)-3-cyano-7-ethoxyquinolin-6-yl)-4-(dimethyl-$d_6$-amino)but-2-enamide, (E)-N-(4-(3-chloro-4-(3-fluorobenzyloxy)phenylamino)-7-(2-methoxyethoxy)quinazolin-6-yl)-4-(dimethyl-$d_6$-amino)but-2-enamide, (E)-N-(4-(3-chloro-4-(3-fluorobenzyloxy)phenylamino)-3-cyano-7-(2-methoxyethoxy)quinolin-6-yl)-4-(dimethyl-$d_6$-amino)but-2-enamide, (E)-N-(4-(3-chloro-4-(pyridin-2-ylmethoxy)phenylamino)-7-(2-methoxyethoxy)quinazolin-6-yl)-4-(dimethyl-$d_6$-amino)but-2-enamide, (E)-N-(4-(3-chloro-4-(pyridin-2-ylmethoxy)phenylamino)-3-cyano-7-(2-methoxyethoxy)quinolin-6-yl)-4-(dimethyl-$d_6$-amino)but-2-enamide, (E)-N-(4-(3-chloro-4-(pyridin-2-ylmethoxy)phenylamino)-7-(2-methoxyethoxy)quinazolin-6-yl)-4-(methyl-$d_3$-methylamino)but-2-enamide, (E)-N-(4-(3-chloro-4-(pyridin-2-ylmethoxy)phenylamino)-3-cyano-7-(2-methoxyethoxy)quinolin-6-yl)-4-(methyl-$d_3$-methylamino)but-2-enamide, (E)-4-(dimethyl-$d_6$-amino)-N-(7-ethoxy-4-(3-ethynylphenylamino)quinazolin-6-yl)but-2-enamide, (E)-N-(3-cyano-7-ethoxy-4-(3-ethynylphenylamino)quinolin-6-yl)-4-(dimethyl-$d_6$-amino)but-2-enamide, (E)-4-(dimethylamino)-N-(7-ethoxy-4-(3-ethynylphenylamino)quinazolin-6-yl)but-2-enamide, (E)-N-(3-cyano-7-ethoxy-4-(3-ethynylphenylamino)quinolin-6-yl)-4-(dimethylamino)but-2-enamide, (E)-4-(dimethyl-$d_6$-amino)-N-(7-ethoxy-4-(3-ethynylphenylamino)quinazolin-6-yl)but-2-enamide, E)-N-(3-cyano-7-ethoxy-4-(3-ethynylphenylamino)quinolin-6-yl)-4-(dimethyl-$d_6$-amino)but-2-enamide, (E)-4-(dimethyl-$d_6$-amino)-N-(7-ethoxy-4-(3-ethynyl-d-phenylamino)quinazolin-6-yl)but-2-enamide, E)-N-(3-cyano-7-ethoxy-4-(3-ethynyl-d-phenylamino)quinolin-6-yl)-4-(dimethyl-$d_6$-amino)but-2-enamide, (E)-N-(3-cyano-7-ethoxy-4-(3-ethynyl-4-(pyridin-2-ylmethoxy)phenylamino)quinolin-6-yl)-4-(dimethyl-$d_6$-amino)but-2-enamide, (E)-N-(3-cyano-7-ethoxy-4-(3-ethynyl-d-4-(pyridin-2-ylmethoxy)phenylamino)quinolin-6-yl)-4-(dimethylamino)but-2-enamide, (E)-N-(3-cyano-7-ethoxy-4-(3-fluoro-4-(pyridin-2-ylmethoxy)phenylamino)quinolin-6-yl)-4-(dimethyl-$d_6$-amino)but-2-enamide, (E)-N-(3-cyano-7-ethoxy-4-(3-methyl-$d_3$-4-(pyridin-2-ylmethoxy)phenylamino)quinolin-6-yl)-4-(dimethylamino)but-2-enamide, (E)-N-(3-cyano-7-ethoxy-4-(3-methoxy-$d_3$-4-(pyridin-2-ylmethoxy)phenylamino)quinolin-6-yl)-4-(dimethylamino)but-2-enamide, (E)-N-(2-chloro-4-(3-cyano-6-(4-(dimethyl-$d_6$-amino)but-2-enamido)-7-ethoxyquinolin-4-ylamino)phenyl)picolinamide, (E)-N-(4-(3-chloro-4-(3-pyridin-2-ylureido)phenylamino)-3-cyano-7-ethoxyquinolin-6-yl)-4-(dimethyl-$d_6$-amino)but-2-enamide, (E)-4-(dimethyl-$d_6$-amino)-N-(7-ethoxy-4-(3-ethynyl-4-(pyridin-2-ylmethoxy)phenylamino)quinazolin-6-yl)but-2-enamide, (E)-4-(dimethyl-$d_6$-amino)-N-(7-ethoxy-4-(3-ethynyl-d-4-(pyridin-2-ylmethoxy)phenylamino)quinazolin-6-yl)but-2-enamide, (E)-4-(methyl-$d_3$-(methyl)amino)-N-(7-ethoxy-4-(3-fluoro-4-(pyridin-2-ylmethoxy)phenylamino)quinazolin-6-yl)but-2-enamide, (E)-4-(dimethylamino)-N-(7-ethoxy-4-(3-methyl-$d_3$-4-(pyridin-2-ylmethoxy)phenylamino)quinazolin-6-yl)but-2-enamide, (E)-4-(dimethylamino)-N-(7-ethoxy-4-(3-methoxy-$d_3$-4-(pyridin-2-ylmethoxy)phenylamino)quinazolin-6-yl)but-2-enamide, (E)-N-(2-chloro-4-(6-(4-(dimethyl-$d_6$-amino)but-2-enamido)-7-ethoxyquinazolin-4-ylamino)phenyl)picolinamide, (E)-N-(7-acetamido-4-(3-chloro-4-(pyridin-2-ylmethoxy)phenylamino)quinazolin-6-yl)-4-(dimethyl-$d_6$-amino)but-2-enamide, (E)-N-(4-(3-chloro-4-(3-pyridin-2-ylureido)phenylamino)-7-ethoxyquinazolin-6-yl)-4-(dimethyl-$d_6$-amino)but-2-enamide, (E)-4-(dimethyl-$d_6$-amino)-N-(7-ethoxy-$d_5$-4-(3-chloro-4-(pyridin-2-ylmethoxy)phenylamino)quinazolin-6-yl)but-2-enamide, and the like.

In some embodiments, the invention compound of Formulas I-III is in the form of pharmaceutically acceptable salt. In certain embodiments, the invention compound of Formulas I-III is a hydrochloride, benzenesulfonate, or methanesulfonate salt. In some embodiments, the invention compound of Formulas I-III is in the form of a solvate. In other embodiments, the compound is in the form of a metabolite. In other embodiments, the invention compound is in the form of a prodrug. In some embodiment, the deuterium enrichment in the selected deuterated compounds is at least about 1%.

In some embodiments provide pharmaceutical compositions comprising a compound of formulas I-III and a pharmaceutically acceptable carrier.

In some embodiments, the compositions are for the treatment of a disease regulated by a protein kinase. In some embodiments, the compositions are for the treatment of a hyper-proliferative disorder and/or angiogenesis disorder.

In some embodiments, the pharmaceutical compositions further comprise an anti-neoplastic agent, an immunosuppressant, an immunostimulant, or combinations thereof. In other embodiments, the pharmaceutical compositions are suitable for oral, parenteral, or intravenous administration.

In some embodiments, the present invention provides methods for regulating the tyrosine kinase signaling transduction comprising administering to a mammalian subject a therapeutically effective amount of a compound of Formulas I-III.

In other embodiments provide herein methods for treating or preventing an EGFR and/or ErbB2 mediated disorder, said method comprises administering to a mammalian subject a therapeutically effective amount of a compound of Formulas I-III.

In other embodiments provide herein methods for treating neoplasia comprising administering to a mammalian subject in need thereof, a therapeutically effective amount of a compound of Formulas I-III. In certain embodiments, the neoplasia is selected from leukemias, colon carcinoma, renal cell carcinoma, gastrointestinal stromal cancer, solid tumor cancer, multiple myeloma, breast cancer, brain cancer, glioblastoma, pancreatic carcinoma, non-small cell lung cancer, non-hodgkin's lymphoma, hepatocellular carcinoma, thyroid cancer, bladder cancer, colorectal cancer, prostate cancer, and the like. In certain embodiments, the neoplasia is non-small cell lung cancer, or breast cancer. In some embodiments, the methods further comprising administering one or more anti-cancer agents.

In some embodiments, there are provided methods for treating or preventing a hyper-proliferative and/or angiogenesis comprising administering to a mammalian subject a therapeutically effective amount of a compound of Formulas I-III.

In some embodiments, certain compounds of Formulas I-III irreversible inhibit a family of tyrosine kinase epidermal growth factor receptors (e.g., erbB1, erbB2, erbB3 and erbB4), which is useful in treating cancer and other diseases associated with undesirable cell proliferation.

In some embodiments, a compound of Formulas I-III inhibits a number of mutants of tyrosine kinase epidermal growth factor receptors (e.g., erbB1, erbB2, erbB3 and erbB4), which is advantageous over current commercial drugs.

In some embodiments, a compound of Formulas I-III has abundance for each designated deuterium atom of at least greater than the natural abundance of deuterium, which is 0.015%. In certain embodiments, the deuterium enrichment in compounds of Formulas I-II and certain deuterated compounds of Formula III is at least above 1%.

In certain embodiments, a compound of this invention has an isotopic enrichment factor for each designated deuterium atom of at least 3500, or at least 4000, or at least 4500, or at least 5000, or at least 5500, or at least 6000, or at least 6333.3, or at least 6466.7, or at least 6633.3.

The term "isotopic enrichment factor" as used herein means the ratio between the isotopic abundance and the natural abundance of a specified isotope.

The term "comprising" is meant to be open-ended, including the indicated component(s), but not excluding other elements.

The term "alkyl" refers to straight chain and branched aliphatic hydrocarbon groups, generally having a specified number of carbon atoms (i.e., $C_1$-$C_8$ alkyl refers to an alkyl group having from 1 to 8 carbon atoms, inclusive). Examples of alkyl groups include, without limitation, methyl, ethyl, n-propyl, i-propyl, n-butyl, s-butyl, t-butyl, n-pentyl, s-pentyl, n-hexyl, and the like.

The term "alkenyl", when used alone or in combination, embraces linear or branched radicals having at least one carbon-carbon double bond in a moiety having between two and ten carbon atoms. Examples of alkenyl radicals include, without limitation, ethenyl, propenyl, allyl, propenyl, butenyl and N,N-dimethylpropenyl. The terms "alkenyl" and "lower alkenyl", embrace radicals having "cis" and "trans" orientations, or alternatively, "E" and "Z" orientations, as appreciated by those of ordinary skill in the art.

The term "alkynyl", when used alone or in combination, denotes linear, cyclic or branched radicals having at least one carbon-carbon triple bond and having two to ten carbon atoms. Examples of such radicals include, without limitation, ethynyl, propynyl (propargyl), butynyl, and the like.

The term "alkoxy" or "alkoxyl", when used alone or in combination, embraces linear or branched oxygen-containing radicals each having alkyl portions of one or more carbon atoms. Examples of such radicals include methoxy, ethoxy, propoxy, butoxy and tert-butoxy, 2-methoxyethoxy, optionally substituted benzyloxy or optionally substituted pyridinylmethoxy, and the like.

The term "optionally substituted alkoxy" means the carbon atom of alkyl portion of the alkoxy group is optionally substituted by H, D, F, Cl, $CF_3$ or $C_1$-$C_6$ alkoxy, $C_1$-$C_6$ alkylamino. The alkyl portion usually having from 1 to 8 carbon atoms.

The term "halo" or "halogen", when used alone or in combination, means halogens such as fluorine, chlorine, bromine or iodine atoms.

The term "aminocarbonyl" when used alone or in combination, denotes nitrogen-containing radicals attached to a carbonyl group substituted by $C_1$-$C_8$ alkyl or $C_2$-$C_8$ alkenyl groups. The each carbon atom of alkyl portion inside the $C_1$-$C_8$ alkyl or $C_2$-$C_8$ alkenyl groups is optionally substituted by H, D, F, Cl, $CF_3$ or $C_1$-$C_6$ alkoxy, $C_1$-$C_6$ alkylamino.

The term "aminoalkyl," "alkylamino," refer, respectively, to $H_2N$-alkyl, alkyl-NH, alkyl-NH-alkyl,(alkyl)$_2$N-alkyl, where alkyl is defined above The term "pharmaceutically acceptable" when used with reference to a compound of Formula I, II or III is intended to refer to a form of the compound that is safe for administration to a subject. For example, a free base, a salt form, a solvate, a hydrate, a prodrug or derivative form of a compound of Formulas I-III, which has been approved for mammalian use, via oral ingestion or any other route of administration, by a governing authority or regulatory agency, such as the Food and Drug Administration (FDA) of the United States, is pharmaceutically acceptable.

Included in the compounds of Formulas I, II and III are the pharmaceutically acceptable salt forms of the free-base compounds. The term "pharmaceutically-acceptable salts" embraces salts, commonly used to form alkali metal salts and to form addition salts of free acids or free bases, which have been approved by a regulatory agency. Salts are formed from ionic associations, charge-charge interactions, covalent bonding, complexation, coordination, etc. The nature of the salt is not critical, provided that it is pharmaceutically acceptable.

Compounds described herein, in some embodiments, are formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, and the like; or with an organic acid, such as, for example, acetic acid, propionic acid, glycolic acid, pyruvic acid, lactic acid, malonic acid, succinic acid, malic acid, maleic acid, fumaric acid, tartaric acid, citric acid, methanesulfonic acid, benzenesulfonic acid, toluenesulfonic acid, gluconic acid, glutamic acid, hydroxynaphthoic acid, salicylic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein, in some embodiments, coordinate with an organic base from basic nitrogen-containing groups, such as, but not limited to, ethanolamine, diethanolamine, triethanolamine, tromethamine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

Additional examples of such salts can be found in Berge et al., J. Pharm. Sci., 66, 1 (1977). Conventional methods, in some embodiments, are used to form the salts. For example, a phosphate salt of a compound of the invention is made by combining the desired compound free base in a desired solvent, or combination of solvents, with phosphoric acid in a desired stoichiometric amount, at a desired temperature, typically under heat (depending upon the boiling point of the solvent). In one embodiment, the salt is precipitated upon cooling (slow or fast) and crystallize (i.e., if crystalline in nature). Further, hemi-, mono-, di, tri- and poly-salt forms of the compounds of the present invention are also contemplated herein. Similarly, hemi-, mono-, di-, tri- and poly-hydrated forms of the compounds, salts and derivatives thereof, are also contemplated herein.

In some embodiments, a compound of Formulas I-III is a hydrochloric, hydrobromic, sulfuric, phosphoric, or metaphosphoric salt or the like. In other embodiments, compounds of Formulas I-III are in a form of a acetic acid salt, propionic acid salt, hexanoic acid salt, cyclopentanepropionic acid salt, glycolic acid salt, pyruvic acid salt, lactic acid salt, malonic acid salt, succinic acid salt, malic acid salt, maleic acid salt, fumaric acid salt, trifluoroacetic acid salt, tartaric acid salt, citric acid salt, benzoic acid, 3-(4-hydroxybenzoyl)benzoic acid salt, cinnamic acid salt, mandelic acid salt, methanesulfonic acid salt, ethanesulfonic acid salt, 1,2-ethanedisulfonic acid salt, 2-hydroxyethanesulfonic acid salt, benzenesulfonic acid salt, toluenesulfonic acid salt, 2-naphthalenesulfonic acid salt, 4-methylbicyclo-[2.2.2]oct-2-ene-1-carboxylic acid salt, glucoheptonic acid salt, 4,4'-methylenebis-(3-hydroxy-2-ene-1-carboxylic acid) salt, 3-phenylpropionic acid salt, trimethylacetic acid salt, tertiary butylacetic acid salt, lauryl sulfuric acid salt, gluconic acid salt, glutamic acid salt, hydroxynaphthoic acid salt, salicylic acid salt, stearic acid salt, muconic acid salt, butyric acid salt, phenylacetic acid salt, phenylbutyric acid salt, valproic acid salt, or the like. In certain embodiments, a compound of Formulas I-III is a hydrochloric, benzenesulfonate, or methanesulfonate salt.

The term "derivative" is broadly construed herein, and intended to encompass any salt of a compound of this invention, any ester of a compound of this invention, or any other compound, which upon administration to a patient is capable of providing (directly or indirectly) a compound of this invention, or a metabolite or residue thereof, characterized by the ability to the ability to modulate a kinase enzyme.

The term "prodrug", as used herein, denotes a compound which upon administration to a subject or patient is capable of providing (directly or indirectly) a compound of this invention. A "pharmaceutically-acceptable prodrug" as used herein, denotes a prodrug, which is pharmaceutically acceptable.

In some embodiments, the compound(s) of Formula I, II or III are used to treat a subject by administering the compound(s) as a pharmaceutical composition. To this end, the compound(s), in one embodiment, are combined with one or more pharmaceutically acceptable excipients, including carriers, diluents or adjuvants, to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective amount" is intended to quantify the amount of each agent, which will achieve the goal of improvement in disorder severity and the frequency of incidence over treatment of each agent by itself, while avoiding adverse side effects typically associated with alternative therapies. The effective amount, in one embodiment, is administered in a single dosage form or in multiple dosage forms.

MS Method

Unless otherwise indicated, all mass spectral data for starting materials, intermediates and/or exemplary compounds are reported as mass/charge (m/z), having an (M+H$^+$) molecular ion. The molecular ion reported was obtained by electrospray detection method. Compounds having an isotopic atom, such as bromine and the like, are reported according to the detected isotopic pattern, as appreciated by those skilled in the art.

Proton NMR Spectra

Unless otherwise indicated, all $^1$H NMR spectra were run on a Bruker series 500 MHz instrument. Where so characterized, all observed protons are reported as parts-per-million (ppm) downfield from tetramethylsilane (TMS) or other internal reference in the appropriate solvent indicated.

All synthetic procedures described herein can be carried out under known reaction conditions, advantageously under those described herein, either in the absence or in the presence (usually) of solvents or diluents. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups in some cases are protected with suitable protecting groups when necessary. Protecting groups, their introduction and removal are described above.

In synthesizing a compound of Formulas I, II and III according to a desired procedure, the steps in some embodiment, are performed in an order suitable to prepare the compound, including a procedure described herein or by an alternate order of steps described herein, and in one embodiment, be preceded, or followed, by additional protection/deprotection steps as necessary. In certain embodiment, the procedures are further use appropriate reaction conditions, including inert solvents, additional reagents, such as bases (e.g., LDA, DIEA, pyridine, K$_2$CO$_3$, and the like), catalysts, and salt forms of the above. The intermediates in some embodiments are isolated or carried on in situ, with or without purification. Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction. Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3$^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, 2$^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

The compounds of this invention in some embodiments also are represented in multiple tautomeric forms. The invention expressly includes all tautomeric forms of the compounds described herein.

The compounds in one embodiment also occur in cis- or trans- or E- or Z-double bond isomeric forms. All such isomeric forms of such compounds are expressly included in the present invention.

Optionally, the compounds of the invention are modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion. By way of example, a compound of the invention is modified to incorporate a hydrophobic group or "greasy" moiety in an attempt to enhance the passage of the compound through a hydrophobic membrane, such as a cell wall.

These detailed descriptions are presented for illustrative purposes only and are not intended as a restriction on the scope of the invention.

Although the pharmacological properties of the compounds of the invention (Formulas I, II and III) vary with structural change, in general, activity possessed by compounds of Formulas I, II and III in one embodiment is demonstrated both in vitro as well as in vivo. Particularly, the pharmacological properties of the compounds of this invention in some embodiments are confirmed by a number of pharmacological in vitro assays. The following exemplified pharmacological assays have been carried out with the compounds according to the invention.

Indication

The present invention provides compounds which are capable of modulating one or more signal transduction pathways comprising, but not limited to, EGFR and/or ErbB2. EGFR and/or ErbB2 is an important signaling molecule involved in the regulation of a number of key cellular processes, including cell growth, cell survival and invasion.

The compounds of the present invention can also modulate one or more of the following processes, including, but not limited to, e.g., cell growth (including, e.g., differentiation, cell survival, and/or proliferation), tumor cell growth (including, e.g., differentiation, cell survival, and/or proliferation), tumor regression, endothelial cell growth (including, e.g., differentiation, cell survival, and/or proliferation) etc.

By the term "modulate," it is meant that the functional activity of the pathway (or a component of it) is changed in comparison to its normal activity in the absence of the compound. This effect includes any quality or degree of modulation, including, increasing, agonizing, augmenting, enhancing, facilitating, stimulating, decreasing, blocking, inhibiting, reducing, diminishing, antagonizing, etc.

In some embodiments, the compounds of the present invention can be used to treat and/or prevent any disease or condition involving one or more cellular signal transduction pathways comprising EGFR and/or ErbB2.

Any tumor or cancer can be treated, including, but not limited to, cancers having one or more mutations in EGFR and/or ErbB2, as well as any upstream or downstream member of the signaling pathways of which they are a part. As discussed earlier, a cancer can be treated with a compound of the present invention irrespective of the mechanism which is responsible for it.

The invention also provides methods for treating, preventing, modulating, etc., diseases and conditions in mammals comprising administering a compound of this invention with another modulator of the signal transduction pathway comprising, but not limited to EGFR and/or ErbB2. These can be present in the same composition or in separate formulations or dosage units. Administration can be the same or different routes, and can be simultaneous, sequential, etc. These methods generally involve administering effective amounts of compounds of the present invention, where an effective amount is the quantity of the compound which is useful to achieve the desired result. Compounds can be administered in any effective form by any effective route, as discussed in more detail below.

Methods include modulating tumor cell proliferation, including inhibiting cell proliferation. The latter indicates that the growth and/or differentiation of tumor cells is reduced, decreased, diminished, slowed, etc. The term "proliferation" includes any process which relates to cell growth and division, and includes differentiation and apoptosis. Any amount of inhibition is considered therapeutic.

Any tumor or cancer can be treated, including, but not limited to, cancers having one or more mutations in EGFR and/or ErbB2, as well as any upstream or downstream member of the signaling pathways of which they are a part. As discussed earlier, a cancer can be treated with a compound of the present invention irrespective of the mechanism which is responsible for it. Cancers of any organ can be treated, including cancers of, but are not limited to, e.g., colon, pancreas, breast, prostate, bone, liver, kidney, lung, testes, skin, pancreas, stomach, colorectal cancer, renal cell carcinoma, hepatocellular carcinoma, melanoma, etc.

Examples of breast cancer include, but are not limited to, invasive ductal carcinoma, invasive lobular carcinoma, ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypophtalmic glioma, cerebellar and cerebral astrocytoma, medulloblastoma, ependymoma, as well as neuroectodermal and pineal tumor.

Tumors of the male reproductive organs include, but are not limited to, prostate and testicular cancer. Tumors of the female reproductive organs include, but are not limited to, endometrial, cervical, ovarian, vaginal, and vulvar cancer, as well as sarcoma of the uterus.

Tumors of the digestive tract include, but are not limited to, anal, colon, colorectal, esophageal, gallbladder, gastric, pancreatic, rectal, small-intestine, and salivary gland cancers.

Tumors of the urinary tract include; but are not limited to, bladder, penile, kidney, renal pelvis, ureter, and urethral cancers.

Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to, squamous cell carcinoma, Kaposi's sarcoma, malignant melanoma, Merkel cell skin cancer, and non-melanoma skin cancer.

Head-and-neck cancers include, but are not limited to, laryngeal, hypopharyngeal, nasopharyngeal, and/or oropharyngeal cancers, and lip and oral cavity cancer.

Lymphomas include, but are not limited to, AIDS-related lymphoma, non-Hodgkin's lymphoma, cutaneous T-cell lymphoma, Hodgkin's disease, and lymphoma of the central nervous system.

Sarcomas include, but are not limited to, sarcoma of the soft tissue, osteosarcoma, malignant fibrous histiocytoma, lymphosarcoma, and rhabdomyosarcoma.

Leukemias include, but are not limited to, acute myeloid leukemia, acute lymphoblastic leukemia, chronic lymphocytic leukemia, chronic myelogenous leukemia, and hairy cell leukemia.

In addition to inhibiting the proliferation of tumor cells, compounds of the present invention can also cause tumor regression, e.g., a decrease in the size of a tumor, or in the extent of cancer in the body.

The present invention relates to a method for using the compounds described above (compounds of Formula I, II, or III), including salts and esters thereof and compositions thereof, to treat mammalian hyper-proliferative disorders and/or angiogenesis disorders (e.g. cancers). This method comprises administering to a mammal in need thereof, including a human, an amount of a compound of this invention, or a pharmaceutically acceptable salt or ester thereof, which is effective to treat the disorder. Hyper-proliferative disorders include but are not limited to cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

The amount of compound(s) which is/are administered and the dosage regimen for treating cancer with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. In some embodiments, a daily dose of about 0.01 to 500 mg/kg, advantageously between about 0.01 and about 50 mg/kg, more advantageously about 0.01 and about 30 mg/kg, even more advantageously between about 0.1 and about 10 mg/kg, and even more advantageously between about 0.25 and about 1 mg/kg body weight are appropriate, and should be useful for all methods of use disclosed herein. The daily dose can be administered in one to four doses per day.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

Pharmaceutical Compositions/Formulations

One embodiment provides a pharmaceutical composition comprising a compound of Formulas I-III, or a stereoisomer, tautomer, hydrate, solvate or pharmaceutically acceptable salt thereof, and at least one pharmaceutically acceptable excipient.

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

Provided herein are pharmaceutical compositions that include a compound of Formulas I-III and at least one pharmaceutically acceptable inactive ingredient. In some embodiments, the compounds described herein are administered as pharmaceutical compositions in which compounds of Formulas I-III are mixed with other active ingredients, as in combination therapy. In other embodiments, the pharmaceutical compositions include other medicinal or pharmaceutical agents, carriers, adjuvants, preserving, stabilizing, wetting or emulsifying agents, solution promoters, salts for regulating the osmotic pressure, and/or buffers. In yet other embodiments, the pharmaceutical compositions include other therapeutically valuable substances.

A pharmaceutical composition, as used herein, refers to a mixture of a compound of Formulas I-III with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, antifoaming agents, antioxidants, preservatives, or one or more combination thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

The pharmaceutical compositions described herein, which include a compound of Formulas I-III are formulated into any suitable dosage form, including but not limited to, aqueous oral dispersions, liquids, gels, syrups, elixirs, slurries, suspensions, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

All formulations for oral administration are in dosages suitable for such administration. Examples of such dosage units are tablets or capsules. In some embodiments, these contain an amount of active ingredient from about 1 to 2000 mg, advantageously from about 1 to 500 mg, and typically from about 5 to 150 mg. A suitable daily dose for a human or other mammal vary widely depending on the condition of the patient and other factors, but, once again, can be determined using routine methods and practices.

In some embodiments, the solid dosage forms disclosed herein are in the form of a tablet, (including a suspension tablet, a fast-melt tablet, a bite-disintegration tablet, a rapid-disintegration tablet, an effervescent tablet, or a caplet), a pill, a powder, a capsule, solid dispersion, solid solution, bioerodible dosage form, controlled release formulations, pulsatile release dosage forms, multiparticulate dosage forms, beads, pellets, granules. In other embodiments, the pharmaceutical formulation is in the form of a powder. In still other embodiments, the pharmaceutical formulation is in the form of a tablet. In other embodiments, pharmaceutical formulations of the compounds of Formulas I-III are in the form of a capsule.

In some embodiments, the pharmaceutical solid oral dosage forms are formulated to provide a controlled release of the compound of Formulas I-III. Controlled release refers to the release of the compound of Formulas I-III from a dosage form in which it is incorporated according to a desired profile over an extended period of time. Such longer periods of response provide for many inherent benefits that are not achieved with the corresponding short acting, immediate release preparations.

In one aspect, liquid formulation dosage forms for oral administration are in the form of aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to the particles of the compound of Formulas I-II, the liquid dosage forms include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

In one embodiment, the aqueous suspensions and dispersions described herein remain in a homogenous state, as defined in The USP Pharmacists' Pharmacopeia (2005 edition, chapter 905), for at least 4 hours. In one embodiment, an aqueous suspension is re-suspended into a homogenous suspension by physical agitation lasting less than 1 minute. In still another embodiment, no agitation is necessary to maintain a homogeneous aqueous dispersion.

In one aspect, a compound of Formulas I-III is formulated into a pharmaceutical composition suitable for intramuscular, subcutaneous, or intravenous injection. In one aspect, formulations suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. In one aspect, the active ingredient is in powder form for constitution with a suitable vehicle, e.g., sterile pyrogen-free water, before use.

In some embodiments, the daily parenteral dosage regimen will be from about 0.1 to about 30 mg/kg of total body weight, preferably from about 0.1 to about 10 mg/kg, and more preferably from about 0.25 mg to 1 mg/kg.

For pulmonary administration, the pharmaceutical composition in one embodiment is administered in the form of an aerosol or with an inhaler including dry powder aerosol. Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

In some embodiments of the present invention, there is provided a method of manufacturing a medicament, the method comprising combining an amount of a compound according to Formula I, II, or III with a pharmaceutically acceptable carrier to manufacture the medicament.

In some embodiments, there is provided a method of manufacturing a medicament for the treatment of cancers, the method comprising combining an amount of a compound according to Formula I, II, or III with a pharmaceutically acceptable carrier to manufacture the medicament.

Combinations

While the compounds of the invention can be dosed or administered as the sole active pharmaceutical agent, they can also be used in combination with one or more compounds of the invention or in conjunction with other agents.

In one embodiment, the therapeutic effectiveness of one of the compounds described herein is enhanced by administration of an adjuvant (i.e., by itself the adjuvant may have minimal therapeutic benefit, but in combination with another therapeutic agent, the overall therapeutic benefit to the patient is enhanced). Or, in some embodiments, the benefit experienced by a patient is increased by administering one of the compounds described herein with another therapeutic agent (which also includes a therapeutic regimen) that also has therapeutic benefit.

In one specific embodiment, a compound of Formulas I-III is co-administered with a second therapeutic agent, wherein the compound of Formulas I-III and the second therapeutic agent modulate different aspects of the disease, disorder or condition being treated, thereby providing a greater overall benefit than administration of either therapeutic agent alone. In some embodiments, the second therapeutic agent is anti-cancer agent.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens can be determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound of Formulas I-III is initiated prior to, during, or after treatment with a second agent described herein, and continues until any time during treatment with the second agent or after termination of treatment with the second agent. It also includes treatments in which a compound of Formulas I-III and the second agent being used in combination are administered simultaneously or at different times and/or at decreasing or increasing intervals during the treatment period. Combination treatment further includes periodic treatments that start and stop at various times to assist with the clinical management of the patient.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills). In one embodiment, one of the therapeutic agents is given in multiple doses, and in another, two (or more if present) are given as multiple doses. In some embodiments of non-simultaneous administration, the timing between the multiple doses varies from more than zero weeks to less than four weeks. In addition, the combination methods, compositions and formulations are not to be limited to the use of only two agents; the use of multiple therapeutic combinations is also envisioned.

In one aspect, the compound of Formulas I-III is administered or formulated in combination with one or more anti-cancer agents. In some embodiments, one or more of the anti-cancer agents are proapoptotic agents. Examples of anti-cancer agents include, but are not limited to, any of the following: gossypol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib, geldanamycin, 17-N-Allylamino-17-Demethoxygeldanamycin (17-AAG), flavopiridol, LY294002, bortezomib, trastuzumab, BAY 11-7082, PKC412, or PD184352, paclitaxel, and analogs of paclitaxel. Compounds that have the basic taxane skeleton as a common structure feature, have also been shown to have the ability to arrest cells in the G2-M phases due to stabilized microtubules and may be useful for treating cancer in combination with the compounds described herein.

Other anti-cancer agents for use in combination with the compounds of Formulas I-III include one or more of the following: abiraterone, adriamycin, dactinomycin, bleomycin, vinblastine, cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL2), interferon alfa-2a; interferon alfa-2b; interferon alfa-n1; interferon alfa-n3; interferon beta-1 a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Yet other anticancer agents for use in combination with the compounds of Formulas I-III include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products for use in combination with the compounds of Formulas I-III include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents for use in combination with the compounds of Formulas I-III include, but are not limited to, nitrogen mustards (e.g., mechloroethamine, cyclophosphamide, chlorambucil, meiphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, etc.).

These detailed descriptions are presented for illustrative purposes only and are not intended as a restriction on the scope of the invention.

SYNTHESIS OF COMPOUNDS

EXAMPLE 1

Preparation of N-(2-hydroxy-4-nitrophenyl)acetamide

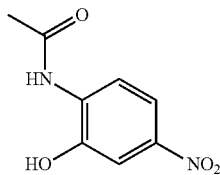

Acetic anhydride (79.6 g, 0.76 mol, 1.46 equiv) was added over 1.5 hours to the mixture of 2-amino-5-nitrophenol (80 g, 0.52 mol, 1.00 equiv) and acetic acid (320 ml, 5.2 mol, 10 equiv) at 60° C. After 1 hour, additional acetic anhydride was added (7.4 g, 0.071 mol, 0.137 equiv). After another 1 hour, the mixture was cooled and diluted with 200 ml of water. Solid was formed and collected by filtration and washed with water and heptane. The solid was dried in a vacuum oven to give the title compound 94 g. MS (ESI) m/z: 197 (M+1).

EXAMPLE 2

Preparation of N-(2-(2-methoxyethoxy)-4-nitrophenyl)acetamide

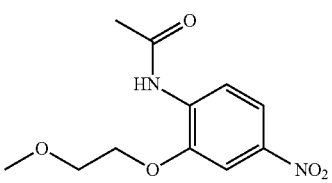

The mixture of N-(2-hydroxy-4-nitrophenyl)acetamide (93 g, 0.47 mol, 1.00 equiv), potassium carbonate (184 g, 1.33 mol, 2.81 equiv) and dimethylformamide (465 ml) was stirred at 60° C. as 2-bromoethyl methyl ether (90 g, 0.647 mol, 1.36 equiv) was added over 15 minutes. After 1 hour, additional 2-bromoethyl methyl ether (4 g, 0.028 mol, 0.059 equiv) was added and the mixture was stirred at 60° C. for another hour. The mixture was cooled to room temperature and poured into 1 L of water. After 30 minutes, the product was formed and collected by filtration and washed with water and heptane. The product was dried in a vacuum oven at 60° C. to give the title compound 97 g. MS (ESI) m/z: 255 (M+1).

EXAMPLE 3

Preparation of (E)-ethyl 3-(4-acetamido-3-(2-methoxyethoxy)phenylamino)-2-cyanoacrylate

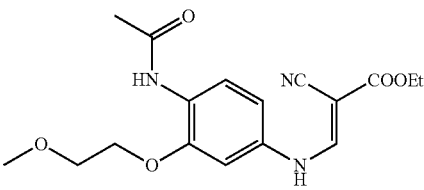 [SMILES: CCOC(=O)/C(C#N)=C/Nc1ccc(NC(C)=O)c(OCCOC)c1]

To N-(2-(2-methoxyethoxy)-4-nitrophenyl)acetamide (75 g, 0.295 mol, 1.00 equiv) was added methanol (600 ml), 10% Pd/C (6 g), and glacial acetic acid (60 ml) in a vessel which subject to a closed pressure vessel. Replacement of Kettle access from air to 5 atm hydrogen at room temperature was deployed and reacted for 5 hours. The reaction mixture was filtered, and concentrated. Toluene (440 ml), THF (220 ml), and (E)-ethyl 2-cyano-3-ethoxyacrylate (76 g, 0.497 mol, 1.68 equiv) were added and then refluxed for 16 h. The reaction mixture was cooled to room temperature, filtered, washed and dried with tetrahydrofuran to give 77 g product as off-white solid. MS (ESI) m/z: 347 (M+1).

EXAMPLE 4

Preparation of N-(3-cyano-4-hydroxy-7-(2-methoxyethoxy)quinolin-6-yl)acetamide

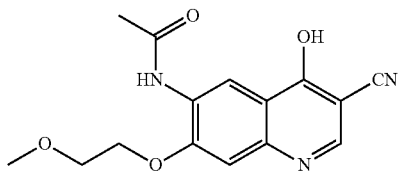 [SMILES: COCCOc1cc2ncc(C#N)c(O)c2cc1NC(C)=O]

A solution of (E)-ethyl 3-(4-acetamido-3-(2-methoxyethoxy)phenylamino)-2-cyanoacrylateb (30 g, 0.0864 mol, 1.00 equiv) in 1.8 L of Dowtherm was stirred under nitrogen at 250° C. for 15 hours. The mixture was cooled to room temperature when precipitate was formed and collected by filtration. The solid was washed with toluene and mixed with tetrahydrofuran (120 ml). The mixture was refluxed for 30 minutes and then cooled to room temperature to yield precipitate. The solid was collected and washed with tetrahydrofuran. After drying 9.0 g of the title compound was obtained. MS (ESI) m/z: 301 (M+1).

EXAMPLE 5

Preparation of N-(4-chloro-3-cyano-7-(2-methoxyethoxy)quinolin-6-yl)acetamide

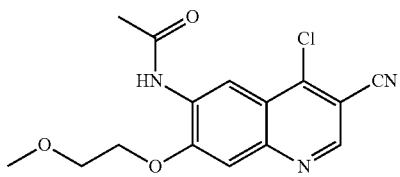 [SMILES: COCCOc1cc2ncc(C#N)c(Cl)c2cc1NC(C)=O]

A stirred mixture of N-(3-cyano-4-hydroxy-7-(2-methoxyethoxy)quinolin-6-yl)acetamide (8.8 g, 0.029 mol, 1.00 equiv) in phosphorus oxychloride (70 mL, 0.765 mol, 26.4 equiv) was heated to 80-85° C. for 4 hours. The reaction mixture was cooled and filtrated. The filtrates were added to a cooled (0-10° C.) solution of potassium carbonate (270 g, 1.95 mol) in 470 ml water. The resulting yellow mixture was stirred for at least 12 hours. The mixture was filtered and washed with hot water. The collected solids were dried to give product 6.5 g. MS (ESI) m/z: 319 (M+1).

EXAMPLE 6

Preparation of 6-amino-4-(3-chloro-4-(pyridin-2-ylmethoxy)phenylamino)-7-(2-methoxyethoxy)quinoline-3-carbonitrile

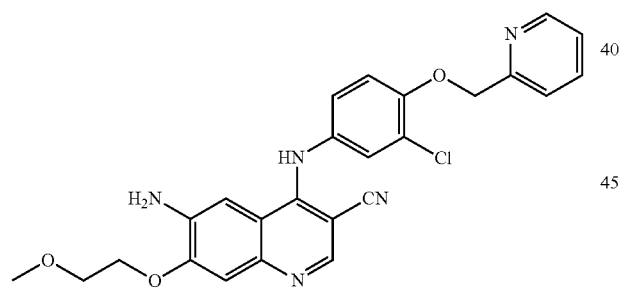

A mixture of N-(4-chloro-3-cyano-7-(2-methoxyethoxy)quinolin-6-yl)acetamide (6.3 g, 0.0197 mol, 1.00 equiv), 3-chloro-4-(2-pyridylmethoxy)aniline (4.7 g, 0.0201 mol, 1.00 equiv), methanesulfonic acid (0.7 ml, 0.0108 mol) and ethanol (150 ml) was stirred under refluxed for 6 hours and then 0.6N hydrogen chloride (300 ml, 0.18 mol) was added. The mixture was heated to 80° C. for 19 hours, and then cooled to 0° C. to form precipitate. The precipitated solids were filtered and then added to a solution of 1N potassium carbonate (100 ml, 0.1 mol) in methanol (150 ml) and then the mixture was stirred for 3 hours. The resulting mixture was filtered, washed with 1:1 methanol/water (300 ml) and dried to give product 6.4 g. MS (ESI) m/z: 475 (M+1).

EXAMPLE 7

Preparation of (E)-N-(4-(3-chloro-4-(pyridin-2-ylmethoxy)phenylamino)-3-cyano-7-2-methoxyethoxy)quinolin-6-yl)-4-(dimethyl-$d_6$-amino)but-2-enamide

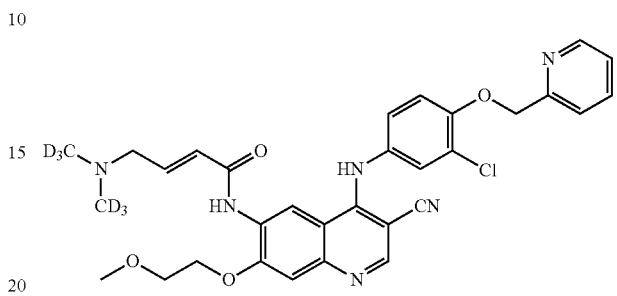

A solution of (E)-4-(dimethyl-$d_6$-amino)but-2-enoic acid hydrochloride (1.28 g, 7.46 mmol, 1.96 equiv) in THF (18 ml) and a catalytic amount of DMF was cooled to 5° C. while oxalyl chloride (0.67 ml, 0.007 mol, 1.84 equiv) was added slowly. The mixture was then warmed to room temperature and stirred for 3 hours. A solution of 6-amino-4-(3-chloro-4-(pyridin-2-ylmethoxy)phenylamino)-7-(2-methoxyethoxy)quinoline-3-carbonitrile (1.8 g, 0.0038 mol, 1 equiv) in N-methyl-2-pyrrolidinone (20 ml) was added dropwise over 10 minutes. The mixture was then stirred for overnight. The reaction was quenched with water and then aqueous sodium hydroxide was added to bring the pH to 11. The resulting mixture was stirred for 1 hour. The precipitate of the reaction mixture was filtered and washed with water; the wet solid was then recrystallized in acetonitrile and THF. The final product was dried to give 1.64 g. MS (ESI) m/z: 592 (M+1).

EXAMPLE 8

Preparation of 2-((2-chloro-4-nitrophenoxy)methyl)pyridine

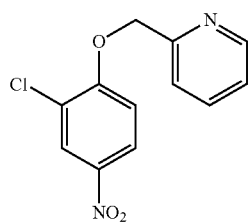

A mixture of potassium hydroxide (20.6 g, 0.15 mol, 0.52 equiv) and 2-pyridylcarbinol (31.08 g, 0.285 mol, 1.00 equiv) in acetonitrile (750 ml) was stirred at 35° C. for 30 minutes. A solution of the 3-chloro-4-fluoronitrobenzene (50 g, 0.29 mol, 1.00 equiv) in acetonitrile (250 ml) was added and the mixture was stirred at 40° C. for 14 hours and then cooled to room temperature. Water (1000 ml) was added and the precipitated solids were filtered and washed with water and dried to give product 52.5 g. MS (ESI) m/z: 265 (M+1).

EXAMPLE 9

Preparation of 3-chloro-4-(pyridin-2-ylmethoxy)aniline

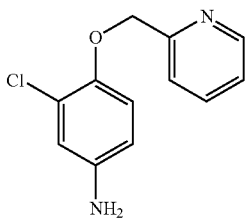 [SMILES: O=[N+]([O-])c1ccc(OCc2ccccn2)c(Cl)c1]

A mixture of 2-((2-chloro-4-nitrophenoxy)methyl)pyridine (26.5 g, 0.10 mol, 1.00 equiv), iron powder (25.2 g, 0.43 mol, 4.28 equiv) and ammonium chloride (72.24 g, 1.35 mol, 13.5 equiv) in ethanol (600 ml) was stirred mechanically under refluxed for 2 hours. The reaction was allowed to cool down; the mixture of the reaction was filtered and the filtrate was taken to dryness in vacuum. The resulted solid was dissolved in methylene chloride (500 ml) and filtered. Removal of the solvent from the filtrate in vacuum gave 15.3 g of the product. MS (ESI) m/z: 235 (M+1).

EXAMPLE 10

Preparation of 6-amino-4-(3-chloro-4-(pyridin-2-ylmethoxy)phenylamino)-7-ethoxyquinoline-3-carbonitrile

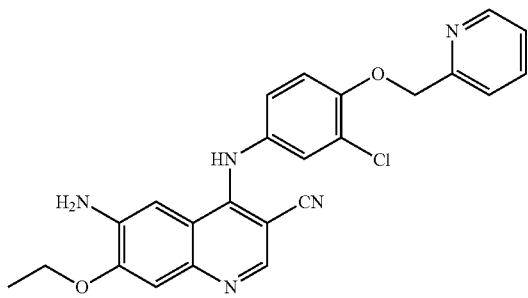 [SMILES: CCOc1cc2ncc(C#N)c(Nc3ccc(OCc4ccccn4)c(Cl)c3)c2cc1N]

A mixture of N-(4-chloro-3-cyano-7-ethoxyquinolin-6-yl)acetamide (11.64 g, 0.04 mol, 1.00 equiv), 3-chloro-4-(pyridin-2-ylmethoxy)aniline (9.53 g, 0.04 mol, 1.00 equiv), methanesulfonic acid (1.3 ml, 0.02 mol, 0.5 equiv) in ethanol (30 ml) was stirred under refluxed for 6 hours and then 0.6N hydrogen chloride (600 ml, 0.36 mol) was added. The mixture was heated to 80° C. for additional 19 hours, and then cooled to 0° C. where the precipitated solids were formed and filtered. The product was added to a solution of 1N potassium carbonate (200 ml, 0.2 mol) in methanol (300 ml) and the resulting mixture was stirred for 3 hours. The resulting precipitated solids were filtered, washed with 1:1 methanol/water (500 ml) and dried to give 12.8 g of product. MS (ESI) m/z: 446 (M+1).

EXAMPLE 11

E-methyl 4-(dimethyl-$d_6$-amino)but-2-enoate hydrochloride

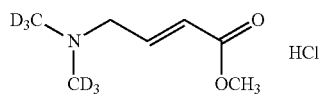

Triethylamine (75 ml, 0.54 mol, 2.8 equiv) was dissolved in THF (200 ml), and dimethyl-$d_6$-amine hydrochloride (20 g, 0.23 mol, 1.2 equiv) was added. Methyl 4-bromocrotonate (40 g, 85% purity, 0.19 mol, 1.00 equiv) in THF (200 ml) was added drop-wise to the solution at room temperature while stirring, and the mixture was allowed to react overnight at room temperature. The resulting solid was filtered and the filtrate was evaporated under reduced pressure to give yellow oil. The oil was dissolved in isopropanol (100 ml) and then hydrogen chloride was added to the solution until pH of 2.0 was reached. The solid product was formed, filtered and dried to give 14.6 g of title compound. MS (ESI) m/z: 149 (M+1).

EXAMPLE 12

Preparation of (E)-4-dimethyl-$d_6$-amino)but-2-enoic acid hydrochloride

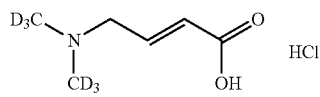

A solution of sodium hydroxide (12.4 g, 0.31 mol, 4.1 equiv) in water (80 ml) was added to a stirred solution of (E)-methyl 4-(dimethyl-$d_6$-amino)but-2-enoate hydrochloride (14 g, 0.0755 mol, 1.00 equiv) in methanol (300 ml). The reaction mixture was stirred for 4 hours and then 6N hydrochloric acid was added to bring the pH to 2. The reaction mixture was concentrated under reduced pressure and then ethanol (100 ml) was added. The resulting solid was removed by filtration. The filtrate was concentrated under reduced pressure to give thick oil. The oil was crystallized in isopropanol and acetone to give the product 7.2 g. MS (ESI) m/z: 135 (M+1).

EXAMPLE 13

Preparation of (E)-N-{4-[3-chloro-4-(2-pyridinyl-methoxy)aniline]-3-cyano-7-ethoxy-6-quinolinyl}-4-(dimethyl-d$_6$-amino)-2-butenamide (Compound A)

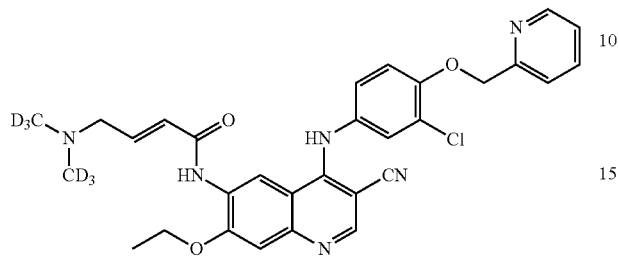

A solution of 4-N,N-dimethyl-d$_6$-ainocrotonic acid hydrochloride (1.28 g, 0.008 mol, 1.96 equiv) in THF (18 ml) and a catalytic amount of DMF was cooled to 5° C. while oxalyl chloride (0.67 ml, 0.007 mol, 1.84 equiv) was slowly added. The mixture was then warmed to room temperature and stirred for 3 hours. A solution of 4-[3-chloro-4-(2-pyridymethoxy)aniline]-3-cyano-7-ethoxy-6-aminoquinoline (1.7 g, 0.004 mol, 1.00 equiv) in N-methyl-2-pyrrolidinone (20 ml) was added dropwise over 10 minutes. The resulting mixture was stirred overnight at room temperature. The reaction was quenched with water and then aqueous sodium hydroxide was added to bring the pH to 11. The mixture was stirred for additional 1 hour. The resulting precipitate was filtered and washed with water. The wet solid was recrystallized in acetonitrile and THF, and dried to give 1.56 g of product. MS (ESI) m/z: 563 (M+1).

EXAMPLE 14

Preparation of 6-amino-7-ethoxy-4-(3-ethynylphenylamino)quinoline-3-carbonitrile

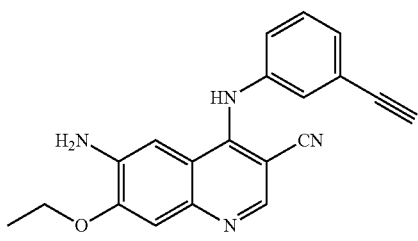 [SMILES: C#Cc1cccc(Nc2c(C#N)cnc3cc(OCC)c(N)cc23)c1]

A mixture of N-(4-chloro-3-cyano-7-ethoxyquinolin-6-yl) acetamide (23.2 g, 0.08 mol, 1.00 equiv), 3-ethynyl aniline (10.1 g, 0.094 mol, 1.18 equiv), methanesulfonic acid (2.3 ml, 0.0355 mol) in ethanol (60 0 ml) was stirred under refluxed for 6 hours and then 0.6N hydrogen chloride (1000 ml, 0.6 mol) was added. The reaction mixture was heated to 80° C. and held for 19 hours, and then cooled to 0° C. to form precipitate. The precipitate was filtered and added to a solution of 1N potassium carbonate (400 ml) in methanol (600 ml) in which the mixture was stirred for 3 hours. The mixture was filtered, washed with 1:1 methanol/water (500 ml) and dried to give 21.3 g of product. MS (ESI) m/z: 563 (M+1).

EXAMPLE 15

Preparation of (E)-N-(3-cyano-7-ethoxy-4-(3-ethynylphenylamino)quinolin-6-yl)-4-(dimethyl-d$_6$-amino)but-2-enamide (Compound B)

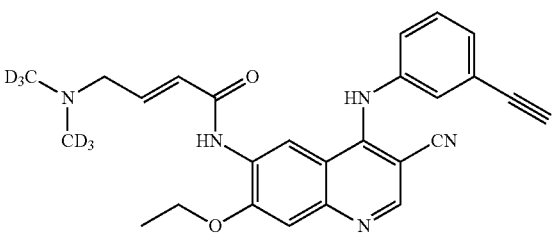 [SMILES: [2H]C([2H])([2H])N(C/C=C/C(=O)Nc1cc2c(Nc3cccc(C#C)c3)c(C#N)cnc2cc1OCC)C([2H])([2H])[2H]]

A solution of (E)-4-(dimethyl-d$_6$-amino)but-2-enoic acid hydrochloride (1.38 g, 0.0076 mol, 2.1 equiv) in THF (18 ml) and a catalytic amount of DMF was cooled to 5° C. while oxalyl chloride (0.67 ml, 0.007 mol, 1.9 equiv) was added slowly. The resulting mixture was then warmed to room temperature and stirred for 3 hours. A solution of 6-amino-7-ethoxy-4-(3-ethynylphenylamino)quinoline-3-carbonitrile (1.2 g, 0.0037 mol, 1.00 equiv) in N-methyl-2-pyrrolidinone (15 ml) was added dropwise over 10 minutes. The reaction mixture was stirred for overnight, and quenched with water (200 ml). Aqueous sodium hydroxide was added to the resulting mixture to bring the pH to 11. The mixture was stirred for 1 hour and the precipitate formed. The resulting precipitate was filtered and washed with water and the wet solid was dried to give 1.48 g product. MS (ESI) m/z: 563 (M+1).

EXAMPLE 16

Preparation of (E)-methyl 4-(dimethylamino)but-2-enoate

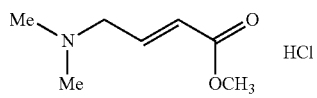

Trithylamine (37.5 ml, 0.27 mol, 2.8 equiv) was dissolved in THF (100 ml), and dimethylamine hydrochloride (9.3 g, 0.114 mol, 1.2 equiv) was added. Methyl 4-bromocrotonate (20 g, 85% purity, 0.095 mol, 1.00 equiv) in 100 ml of THF was added drop-wise to the resulting solution at room temperature while stirring. The reaction mixture was allowed to react overnight at room temperature. The reaction mixture was filtered, and the filtrate was evaporated under reduced pressure to give yellow oil. The oil was dissolved in 50 ml of isopropanol, and hydrogen chloride was added until pH 2.0 was reached. The white solid was formed and filtered and dried to give 7.1 g product. MS (ESI) m/z: 563 (M+1).

EXAMPLE 17

Preparation of (E)-4-(dimethylamino)but-2-enoic acid hydrochloride

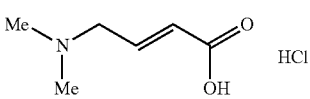

A solution of sodium hydroxide (6.2 g, 0.155 mol, 4 equiv) in water (40 ml) was added to a stirred solution of (E)-methyl 4-(dimethylamino)but-2-enoate hydrochloride (7 g, 0.039 mol, 1.00 equiv) in methanol (150 ml). The reaction mixture was stirred for 4 hours. 6N hydrochloric acid was added to bring the pH to 2. The reaction mixture was concentrated under reduced pressure, and ethanol (50 ml) was added and the solid was removed by filtration. The filtrate was concentrated under reduced pressure to thick oil. The oil was crystallized in isopropanol and acetone to give the product 3.6 g. MS (ESI) m/z: 563 (M+1).

EXAMPLE 18

Preparation of (E)-N-(3-cyano-7-ethoxy-4-(3-ethynylphenylamino)quinolin-6-yl)-4-(dimethylamino)but-2-enamide (Compound C)

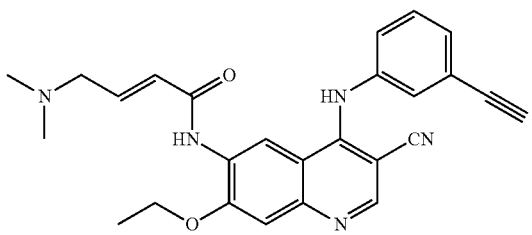 [SMILES: C#Cc1cccc(Nc2c(C#N)cnc3cc(OCC)c(NC(=O)/C=C/CN(C)C)cc23)c1]

A solution of (E)-4-(dimethylamino)but-2-enoic acid hydrochloride (1.28 g, 7.73 mmol, 2.1 equiv) in THF (18 ml) and a catalytic amount of DMF was cooled to 5° C. while oxalyl chloride (0.67 ml, 0.007 mol, 1.9 equiv) was added slowly. The reaction mixture was then warmed to room temperature and stirred for 3 hours. A solution of 6-amino-7-ethoxy-4-(3-ethynylphenylamino)quinoline-3-carbonitrile (1.2 g, 3.66 mmol, 1.00 equiv) in N-methyl-2-pyrrolidinone (15 ml) was added dropwise over 10 minutes. The mixture was stirred for overnight, quenched with water (200 ml). Aqueous sodium hydroxide was added to bring the pH to 11. The mixture was stirred for 1 hour which formed precipitate. The resulting precipitate was filtered and washed with water and the wet solid was dried to give 1.43 g product. MS (ESI) m/z: 563 (M+1).

EXAMPLE 19

Preparation of 4-chloro-7-methoxyquinazolin-6-yl acetate

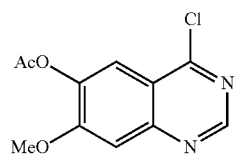 [SMILES: COc1cc2ncnc(Cl)c2cc1OC(C)=O]

A mixture of 7-methoxy-4-oxo-3,4-dihydroquinazolin-6-yl acetate (8.7 g, 0.037 mol), thionyl chloride (120 ml, 1.65 mol) and DMF (1 ml) was stirred and heated to 55° C. for 6 hours. The mixture was cooled to room temperature and thionyl chloride was evaporated. The solid was dissolved in chloroform and the solution was washed with sodium bicarbonate and brine, the chloroform was evaporated under reduced pressure to give 7.9 g of a gray product. MS (ESI) m/z: 253 (M+1).

EXAMPLE 20

Preparation of 4-(3-ethynylphenylamino)-7-methoxyquinazolin-6-yl acetate hydrochloride

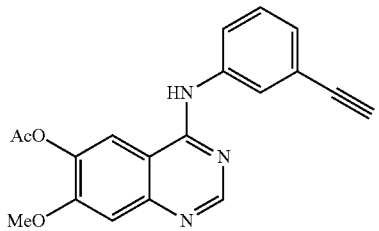 [SMILES: C#Cc1cccc(Nc2ncnc3cc(OC)c(OC(C)=O)cc23)c1]

A mixture of 4-chloro-7-methoxyquinazolin-6-yl acetate (7.75 g, 0.0307 mol), 3-ethynyl aniline (4 g, 0.0342 mol, 1.11 equiv) and chloroform (120 ml) was refluxed overnight. The reaction mixture was cooled to room temperature and the solution was filtered to give 10.2 g product. MS (ESI) m/z: 334 (M+1).

EXAMPLE 21

Preparation of 4-(3-ethynylphenylamino)-7-methoxyquinazolin-6-ol

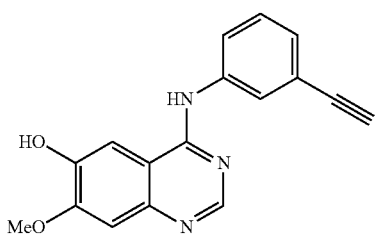 [SMILES: C#Cc1cccc(Nc2ncnc3cc(OC)c(O)cc23)c1]

A mixture of 4-(3-ethynylphenylamino)-7-methoxyquinazolin-6-yl acetate hydrochloride (10 g, 0.027 mol), methanol (250 ml) and 25% aqueous ammonia (8 ml, 0.106 mol, 3.93 equiv) was stirred at room temperature for 17 hours and then heated to reflux for 1.5 hours. The mixture was cooled and the precipitate was formed and isolated and dried to give 5.66 g product. MS (ESI) m/z: 307 (M+1).

EXAMPLE 22

Preparation of N-(3-ethynylphenyl)-7-methoxy-6-(2-methoxyethoxy)quinazolin-4-amine

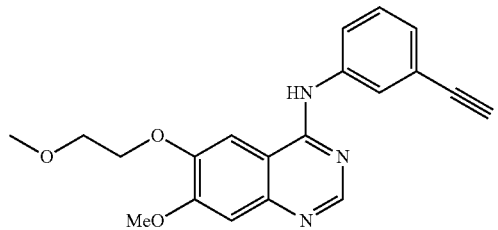 [SMILES: C#Cc1cccc(Nc2ncnc3cc(OC)c(OCCOC)cc23)c1]

A solution of 4-(3-ethynylphenylamino)-7-methoxyquinazolin-6-ol (2.9 g, 0.01 mol), 2-methoxyethyl methane sulfonate (4.6 g, 0.03 mol, 3 equiv), and cesium carbonate (9.9 g, 0.03 mol, 3 equiv) in DMF (100 ml) was heated to 60° C. for 12 hours. The reaction mixture was cooled to room temperature and poured into cold water, the solid was filtrated and dried to give 1.5 g product. MS (ESI) m/z: 350 (M+1).

EXAMPLE 23

Preparation of N-(3-ethynyl-d-phenyl)-7-methoxy-6-(2-methoxyethoxy)quinazolin-4-amine

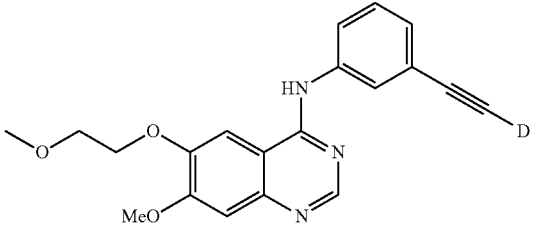 [SMILES: [2H]C#Cc1cccc(Nc2ncnc3cc(OC)c(OCCOC)cc23)c1]

To a solution of N-(3-ethynylphenyl)-7-methoxy-6-(2-methoxyethoxy)quinazolin-4-amine (0.35 g, 0.001 mol) in THF (30 ml) at 0° C. was added isopropyl magnesium chloride (2N in THF, 5 ml, 0.01 mol, 10 equiv). The reaction mixture was stirred at 0° C. for 3 hours and CD$_3$OD (5 ml, 0.12 mol) was added. The reaction mixture was stirred for overnight at room temperature and quenched with D$_2$O and extracted with ethyl acetate. The organic extract was washed with water, dried over Na$_2$SO$_4$ and evaporated to give 0.21 g product. MS (ESI) m/z: 351 (M+1).

EXAMPLE 24

Preparation of 2-methoxy-d$_3$-ethanol

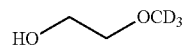

The mixture of Methanol-d$_4$ (20 ml, 0.493 mol, 4 equiv), borontrifluoride diethyl ether complex (0.316 g) and ethylene oxide (5.5 g, 0.125 mol, 1 equiv) was stirred under nitrogen protection for 3 hours, then the Methanol-d$_4$ solution of potassium hydroxide was added to bring the pH to 8-9; methanol-d$_4$ was distilled at atmospheric pressure and the residue was distilled at 140° C. to give 4.2 g 2-d$_3$-methoxyethanol. MS (ESI) m/z: 80 (M+1).

EXAMPLE 25

Preparation of 2-methoxyethyl methanesulfonate

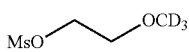

To a solution of 2-d$_3$-methoxyethanol (1.40 g, 18.4 mmol) and triethyl amine (2.40 mL) in methylene chloride (25 mL) at 0° C. was added methanesulfonylchloride (2.05 g, 18.5 mmol) and stirred at 0° C. for 2 h. The reaction mixture was washed with aqueous NaHCO$_3$ and brine, dried over Na$_2$SO$_4$ and concentrated under reduced pressure to give 1.01 g product. MS (ESI) m/z: 158 (M+1).

EXAMPLE 26

Preparation of N-(3-ethynylphenyl)-7-methoxy-6-(2-methoxy-d$_3$-ethoxy)quinazolin-4-amine

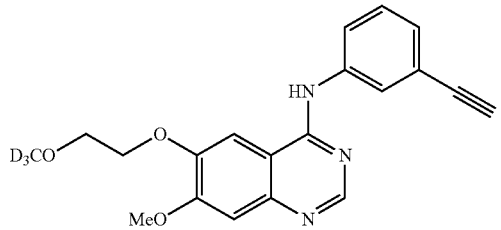

A solution of 4-(3-ethynylphenylamino)-7-methoxyquinazolin-6-ol (0.5 g, 1.7 mmol), 2-d$_3$-methoxyethyl-methane sulfonate (0.75 g, 5.1 mmol), and cesium carbonate (1.50 g, 4.6 mmol) in DMF (12.5 mL) was heated to 60° C. for 12 h. The reaction mixture was cooled to room temperature and poured into cold water. The solid was filtrated and dried to give 180 mg product. MS (ESI) m/z: 353 (M+1).

EXAMPLE 27

Radiometric Kinase Assay

Reagents and Procedure

Base Reaction buffer: 20 mM Hepes (pH 7.5), 10 mM MgCl$_2$, 1 mM EGTA, 0.02% Brij35, 0.02 mg/ml BSA, 0.1 mM Na$_3$VO$_4$, 2 mM DTT, 1% DMSO. *Required cofactors are added individually to each kinase reaction Prepare indicated substrate in freshly prepared Base Reaction Buffer Deliver any required cofactors to the substrate solution above Deliver indicated kinase into the substrate solution and gently mix Deliver compounds in DMSO into the kinase reaction mixture Deliver $^{33}$P-ATP (specific activity 0.01 µCi/µl final) into the reaction mixture to initiate the reaction. The final reaction volume is 5 ul.

Incubate kinase reaction for 120 min. at room temperature

Reactions are spotted onto P81 ion exchange paper (Whatman #3698-915)

Wash filters extensively in 0.1% Phosphoric acid.

Analyze the data for IC50 generation using the sigmoidal dose response (variable slope) algorithm in the program Prism (GraphPad Software, Inc., La Jolla, Calif.)

Kinase Information

EGFR—Genbank Accession # NP_005219.2. Recombinant catalytic domain, amino acids 668-1210, GST tagged, purified from insect cells. Activated in vitro via autophosphorylation. Final concentration in assay=4 nM. Substrate: pEY. Peptide sequence: Poly Glu-Tyr, 4:1 ratio. Final concentration in assay=0.2 mg·mL. 2 mM MnCl2 is added as a cofactor to the reaction mixture ErbB2/HER2—Genbank Accession # X03363. Recombinant catalytic domain, amino acids 679-1255, GST tagged, purified from insect cells. Final concentration in assay=50 nM. Substrate: pEY. Peptide sequence: Poly Glu-Tyr, 4:1 ratio. Final concentration in assay=0.2 mg·mL. 2 mM MnCl2 is added as a cofactor to the reaction mixture Biological Evaluation Compounds in accordance with the practice of the present invention were tested in kinase assays employing high throughput radiometric techniques and nanoliter volume technology (Reaction Biology Corporation, Malvern Pa.). Exemplary Compound A (see Example 13) was tested in 10-dose IC50 mode with 3-fold serial dilution starting at 10 µM. The result showed that exemplary compound A is a potent inhibitor of both EGFR and ErbB2 (HER2). Similarly, other invention compounds such as the compounds from Examples 7, 15 (Compound B), and 18 (Compound C) all found to have potency (IC50)<1 uM over EGFR and Her-2 assays.

| Kinase: | Exemplary Compound A (IC50) |
|---|---|
| EGFR | 1.08 nM |
| ErbB2 | 4.98 nM |

Invention compounds were tested in human tumor cell-line growth assays. For example, Compound C prepared according to Example 18 was found to inhibit the growth of several solid tumor cell-lines, e.g., A431 (reportedly overexpressing EGFR); NCI-H1975 (reportedly expressing the EGFR mutant L858R/T790M); NCI-H1650 (reportedly expressing the EGFR mutant E746-A750); BT-474 (reportedly overexpressing ErbB2); as well as SKBR3 and A549 (both reportedly overexpressing EGFR and ErbB2) under the condition of 10-dose IC50 mode with 3-fold serial dilution starting at 10 µM.

| Exemplary cell line | Compound C (IC50) |
|---|---|
| A431 | <1 mM |
| NCI-H1975 | <10 mM |
| NCI-H1650 | <10 mM |
| BT-474 | <1 mM |
| SKBR3 | <1 mM |
| A549 | <1 mM |

Compared to Compound C, Compound B (the deuterated version of Compound C) was found to show a better pharmacokinetic profile. For example, Compound B exhibited a slower clearance and prolonged $T_{1/2}$ than Compound C. Following the IV administration to Sprague-Dawley rats, the mean elimination half-life ($T_{1/2}$) of Compound B and C was calculated to be 8.76 h and 5.37 h respectively. The mean Clearance (CL) for Compound B is 2824 mL/h/kg, while the corresponding value for Compound C is 3580 mL/h/kg.

Similarly, compared to HKI272, exemplary Compound A was also found to show a better pharmacokinetic profile. For example, following the IV administration to Sprague-Dawley rats, the mean elimination half-life ($T_{112}$) of Compound A and HKI272 was calculated to be 6.59 h and 5.28 h respectively.

What is claimed is:

1. A compound of Formula I:

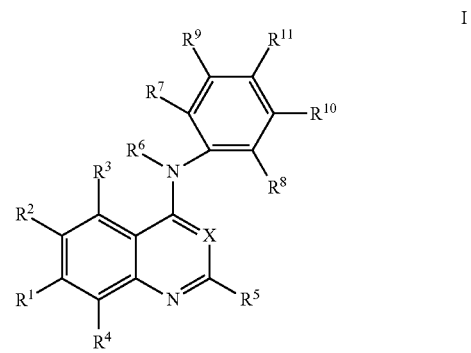

or a pharmaceutically acceptable salt, or solvate thereof, wherein $R^1$ and $R^2$ are independently selected from hydrogen, deuterium, halogen, trifluoromethyl, optionally substituted alkoxy, optionally substituted deuterated alkoxy and optionally substituted aminocarbonyl;

X is C—CN;

$R^3$ to $R^6$ are independently hydrogen (H) or deuterium (D);

$R^7$-$R^{10}$ are independently selected from hydrogen, deuterium, CH$_3$, CD$_3$, CH$_2$D, CHD$_2$, halogen, cyano, trifluoromethyl, optionally substituted alkoxy, optionally substituted deuterated alkoxy, optionally substituted $C_2$-$C_6$ alkynyl and optionally substituted deuterated $C_2$-$C_6$ alkynyl; and $R^{11}$ is hydrogen, deuterium, halogen, trifluoromethyl, optionally substituted alkoxy, optionally substituted deuterated alkoxy, optionally substituted aminocarbonyl, or urea;

provided that $R^1$ to $R^{11}$ contain at least one deuterium atom.

2. The compound of claim 1, wherein $R^1$ and $R^2$ are independently selected from optionally substituted alkoxy, optionally substituted deuterated alkoxy, and optionally substituted aminocarbonyl.

3. The compound of claim 1, wherein $R^9$ and $R^{10}$ are independently selected from halogen, optionally substituted $C_2$-$C_6$ alkynyl and optionally substituted deuterated $C_2$-$C_6$ alkynyl.

4. The compound of claim 1, wherein $R^{11}$ is substituted benzyloxy or pyridinylmethoxy.

5. The compound of claim 1, wherein
$R^1$ is selected from methoxy, methoxy-$d_3$, ethoxy, ethoxy-$d_3$, 2-methoxyethoxy, and
2-methoxy-$d_3$-ethoxy;
$R^2$ is:

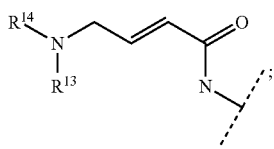

$R^3$-$R^9$ are hydrogen;

$R^{10}$ is selected from hydrogen, deuterium, $CH_3$, $CD_3$, $CH_2D$, $CHD_2$, F, Cl, $CF_3$, CN, ethynyl and ethynyl-d;

$R^{11}$ is selected from hydrogen, deuterium, $CH_3$, $CD_3$, $CH_2D$, $CHD_2$, F, Cl, $CF_3$, 3-fluorobenzyloxy, and pyridin-2-ylmethoxy;

$R^{13}$ and $R^{14}$ are independently selected from hydrogen, deuterium, $CH_3$, $CD_3$, $CH_2D$, and $CHD_2$; and provided that $R^1$, $R^{10}$, $R^{11}$, $R^{13}$, and $R^{14}$ contain at least one deuterium atom.

6. The compound of claim 5, wherein $R^{10}$ is Cl ethynyl or ethynyl-d.

7. The compound of claim 5, wherein $R^{11}$ is 3-fluorobenzyloxy or pyridin-2-ylmethoxy.

8. The compound of claim 5, wherein $R^{13}$ and $R^{14}$ are independently selected from $CH_3$, and $CD_3$.

9. The compound of claim 1, wherein
$R^1$ is $R^{15}O$—;
$R^2$ is:

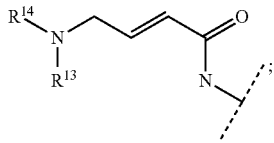

$R^3$-$R^9$ are hydrogen;
$R^{10}$ is ethynyl or ethynyl-d;
$R^{11}$ is hydrogen;
$R^{13}$ and $R^{14}$ are independently selected from hydrogen, deuterium, $CH_3$, $CD_3$, $CH_2D$, and $CHD_2$; and
$R^{15}$ is $C_1$-$C_6$ alkyl or $C_1$-$C_6$ deuterated alkyl.

10. A compound of Formula III:

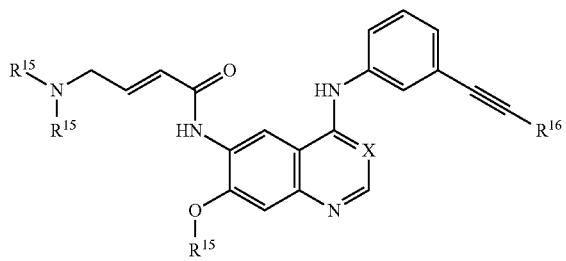

or a pharmaceutically acceptable salt, or solvate thereof, wherein
X is C—CN;
$R^{15}$ is $C_1$-$C_6$ alkyl or $C_1$-$C_6$ deuterated alkyl; and
$R^{16}$ is hydrogen or deuterium.

11. A compound or its pharmaceutically acceptable salt, or solvate thereof selected from the group consisting of:
(E)-N-(4-(3-chloro-4-(pyridin-2-ylmethoxy)phenylamino)-3-cyano-7-ethoxyquinolin-6-yl)-4-(dimethyl-$d_6$-amino)but-2-enamide,
(E)-N-(4-(3-chloro-4-(pyridin-2-ylmethoxy)phenylamino)-3-cyano-7-ethoxyquinolin-6-yl)-4-(methyl-$d_3$-(methyl)amino)but-2-enamide,
(E)-N-(4-(3-chloro-4-(3-fluorobenzyloxy)phenylamino)-3-cyano-7-ethoxyquinolin-6-yl)-4-(methyl-$d_3$-(methyl)amino)but-2-enamide,
(E)-N-(4-(3-chloro-4-(3-fluorobenzyloxy)phenylamino)-3-cyano-7-ethoxyquinolin-6-yl)-4-(dimethyl-$d_6$-amino)but-2-enamide,
(E)-N-(4-(3-chloro-4-(3-fluorobenzyloxy)phenylamino)-3-cyano-7-(2-methoxyethoxy)quinolin-6-yl)-4-(dimethyl-$d_6$-amino)but-2-enamide,
(E)-N-(4-(3-chloro-4-(pyridin-2-ylmethoxy)phenylamino)-3-cyano-7-(2-methoxyethoxy)quinolin-6-yl)-4-(dimethyl-$d_6$-amino)but-2-enamide,
(E)-N-(4-(3-chloro-4-(pyridin-2-ylmethoxy)phenylamino)- 3-cyano-7-(2-methoxyethoxy)quinolin-6-yl)-4-(methyl-$d_3$-methylamino)but-2-enamide
(E)-N-(3-cyano-7-ethoxy-4-(3-ethynylphenylamino)quinolin-6-yl)-4-(dimethyl-$d_6$-amino)but-2-enamide,
(E)-N-(3-cyano-7-ethoxy-4-(3-ethynylphenylamino)quinolin-6-yl)-4-(dimethylamino)but-2-enamide,
(E)-N-(3-cyano-7-ethoxy-4-(3-ethynylphenylamino)quinolin-6-yl)-4-(dimethyl-$d_6$-amino)but-2-enamide,
(E)-N-(3-cyano-7-ethoxy-4-(3-ethynyl-d-phenylamino)quinolin-6-yl)-4-(dimethyl-$d_6$-amino)but-2-enamide,
(E)-N-(3-cyano-7-ethoxy-4-(3-ethynyl-4-(pyridin-2-ylmethoxy)phenylamino)quinolin-6-yl)-4-(dimethyl-$d_6$-amino)but-2-enamide,
(E)-N-(3-cyano-7-ethoxy-4-(3-ethynyl-d-4-(pyridin-2-ylmethoxy)phenylamino)quinolin-6-yl)-4-(dimethylamino)but-2-enamide,
(E)-N-(3-cyano-7-ethoxy-4-(3-fluoro-4-(pyridin-2-ylmethoxy)phenylamino)quinolin-6-yl)-4-(dimethyl-$d_6$-amino)but-2-enamide,
(E)-N-(3-cyano-7-ethoxy-4-(3-methyl-$d_3$-4-(pyridin-2-ylmethoxy)phenylamino)quinolin-6-yl)-4-(dimethylamino)but-2-enamide,
(E)-N-(3-cyano-7-ethoxy-4-(3-methoxy-$d_3$-4-(pyridin-2-ylmethoxy)phenylamino)quinolin-6-yl)-4-(dimethylamino)but-2-enamide, (E)-N-(2-chloro-4-(3-cyano-6-(4-(dimethyl-$d_6$-amino)but-2-enamido)-7-ethoxyquinolin-4-ylamino)phenyl)picolinamide, and (E)-N-(4-(3-chloro-4-(3-pyridin-2-ylureido)phenylamino)-3-cyano-7-ethoxyquinolin-6-yl)-4-(dimethyl-$d_6$-amino)but-2-enamide.

12. A composition comprising a compound according to claim 1 or a pharmaceutically acceptable salt thereof and a pharmaceutically acceptable carrier, diluent, stabilizer or excipient.

* * * * *